United States Patent
Black et al.

(10) Patent No.: US 12,370,010 B2
(45) Date of Patent: Jul. 29, 2025

(54) HOLOGRAPHIC AUGMENTED REALITY ULTRASOUND NEEDLE GUIDE FOR INSERTION FOR PERCUTANEOUS SURGICAL PROCEDURES

(71) Applicant: MEDIVIEW XR, INC., Cleveland, OH (US)

(72) Inventors: John Black, Bowling Green, OH (US); Greg Hart, Hayden, ID (US); Mina S. Fahim, New Brighton, MN (US)

(73) Assignee: MEDIVIEW XR, INC., Cleveland, OH (US)

( * ) Notice: Subject to any disclaimer, the term of this patent is extended or adjusted under 35 U.S.C. 154(b) by 503 days.

(21) Appl. No.: 17/110,991

(22) Filed: Dec. 3, 2020

(65) Prior Publication Data

US 2021/0161612 A1 Jun. 3, 2021

Related U.S. Application Data

(60) Provisional application No. 63/025,584, filed on May 15, 2020, provisional application No. 62/942,857, filed on Dec. 3, 2019.

(51) Int. Cl.
*A61B 17/34* (2006.01)
*A61B 34/20* (2016.01)
(Continued)

(52) U.S. Cl.
CPC .......... *A61B 90/36* (2016.02); *A61B 17/3403* (2013.01); *A61B 34/20* (2016.02);
(Continued)

(58) Field of Classification Search
CPC ..... A61B 90/36; A61B 17/3403; A61B 34/20; A61B 2017/00119; A61B 2017/3407;
(Continued)

(56) References Cited

U.S. PATENT DOCUMENTS 6,546,279 B1 * 4/2003 Bova ............... A61B 90/17
600/439
6,671,538 B1 * 12/2003 Ehnholm ............ A61B 34/20
600/425

(Continued)

FOREIGN PATENT DOCUMENTS

JP 2000500031 A 1/2000
JP 2009529951 A 8/2009
(Continued)

OTHER PUBLICATIONS https://microsoft.github.io/MixedRealityToolkit-Unity/Documentation/README_Interactable.html.

*Primary Examiner* — Amal Aly Farag
(74) *Attorney, Agent, or Firm* — Jacob M. Ward; Ward Law Office LLC

(57) ABSTRACT

A holographic augmented reality ultrasound needle guide system and method includes an augmented reality display such as a headset wearable by a user. The augmented reality display is configured to depict a virtual ultrasound image. The augmented reality display is further configured to allow a user to select a desired reference point on the virtual ultrasound image. The system is configured to depict a holographic needle guide based on the selection of the desired reference point. The system is also configured to adjust a trajectory of the holographic needle guide to avoid intersecting undesired anatomical structures. The augmented reality display is further configured to stamp the holographic needle guide into a selectively locked trajectory and position.

18 Claims, 9 Drawing Sheets

(51) Int. Cl.
*A61B 90/00* (2016.01)
*G06F 3/01* (2006.01)
*A61B 17/00* (2006.01)
*A61B 90/50* (2016.01)

(52) U.S. Cl.
CPC ..... *G06F 3/011* (2013.01); *A61B 2017/00119* (2013.01); *A61B 2017/3407* (2013.01); *A61B 2017/3413* (2013.01); *A61B 2034/2051* (2016.02); *A61B 2034/2055* (2016.02); *A61B 2090/365* (2016.02); *A61B 2090/378* (2016.02); *A61B 2090/3979* (2016.02); *A61B 2090/3995* (2016.02); *A61B 2090/502* (2016.02)

(58) Field of Classification Search
CPC .... A61B 2017/3413; A61B 2034/2051; G06F 3/011
See application file for complete search history.

(56) References Cited

U.S. PATENT DOCUMENTS

| | | | |
|---|---|---|---|
| 2011/0046483 A1* | 2/2011 | Fuchs | A61B 18/1477 606/20 |
| 2014/0128881 A1* | 5/2014 | Tyc | A61B 18/1492 606/20 |
| 2017/0020558 A1 | 1/2017 | Xu et al. | |
| 2017/0258526 A1* | 9/2017 | Lang | A61B 17/1742 |
| 2018/0116731 A1* | 5/2018 | State | A61B 17/07207 |
| 2018/0116732 A1 | 5/2018 | Lin et al. | |
| 2018/0185100 A1* | 7/2018 | Weinstein | A61F 2/461 |
| 2018/0250078 A1* | 9/2018 | Shochat | A61B 17/3403 |
| 2018/0286132 A1 | 10/2018 | Cvetko et al. | |
| 2018/0303563 A1 | 10/2018 | West et al. | |
| 2019/0056693 A1 | 2/2019 | Gelman et al. | |
| 2019/0060001 A1* | 2/2019 | Kohli | A61B 34/20 |
| 2019/0254753 A1* | 8/2019 | Johnson | A61B 34/30 |
| 2019/0282262 A1* | 9/2019 | Bouazza-Marouf | A61B 17/3403 |
| 2019/0339525 A1 | 11/2019 | Yanof et al. | |

FOREIGN PATENT DOCUMENTS

| | | |
|---|---|---|
| JP | 2011200533 A | 10/2011 |
| JP | 2011206281 A | 10/2011 |
| JP | 2013118998 A | 6/2013 |
| JP | 2017153827 A | 9/2017 |
| JP | 2019017656 A | 2/2019 |
| WO | 2019/136412 A1 | 7/2019 |

* cited by examiner

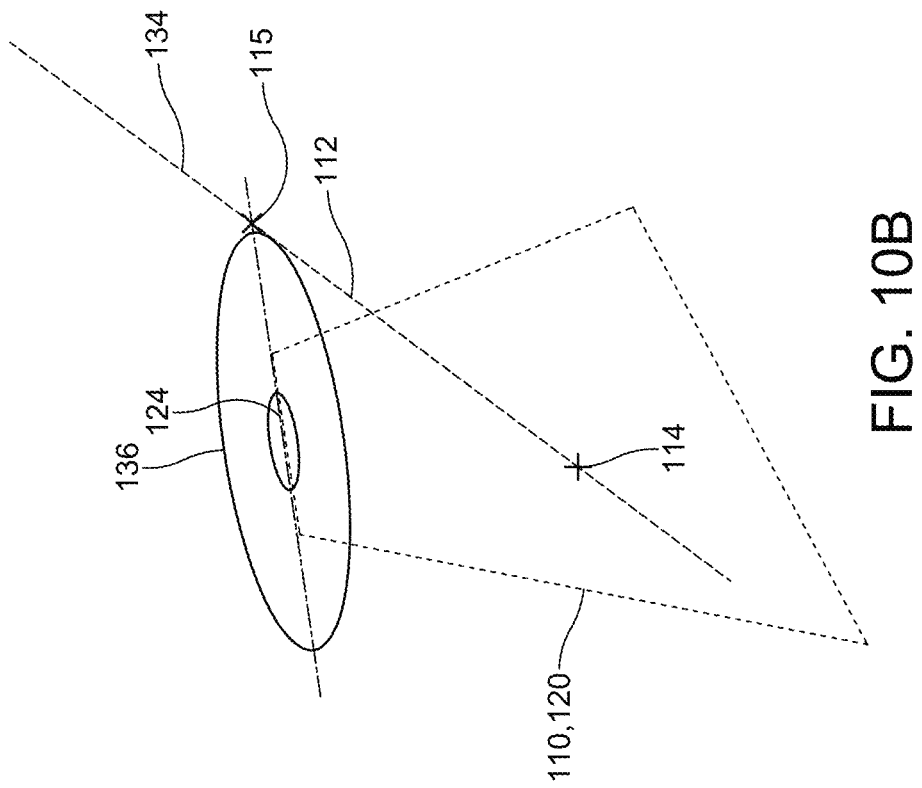
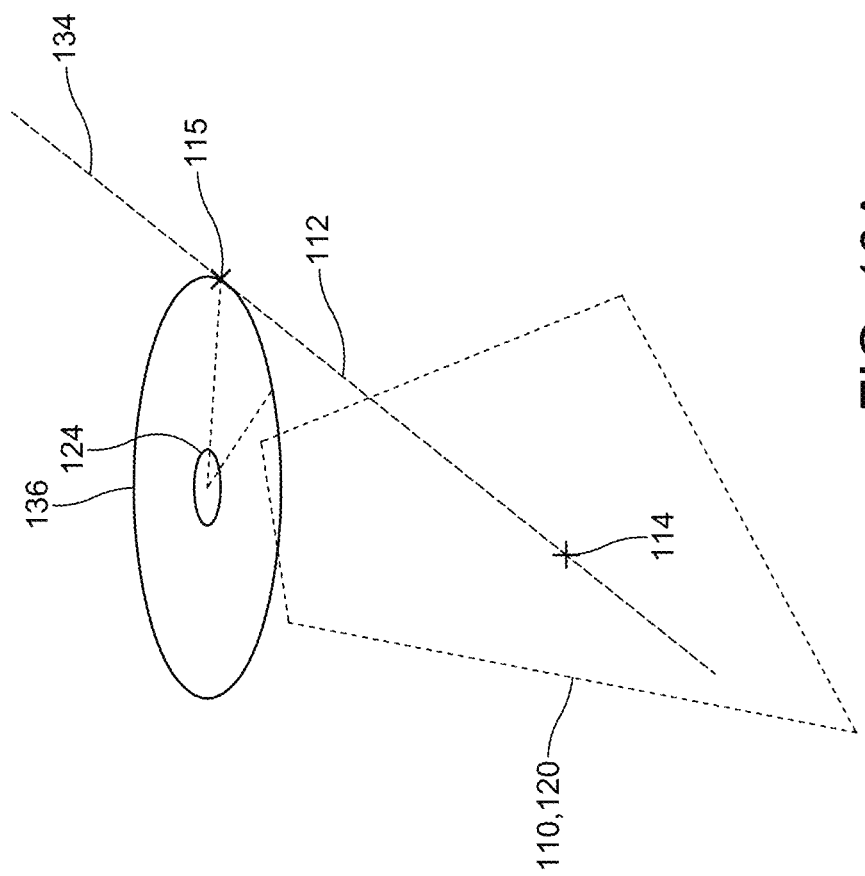

HOLOGRAPHIC AUGMENTED REALITY ULTRASOUND NEEDLE GUIDE FOR INSERTION FOR PERCUTANEOUS SURGICAL PROCEDURES

CROSS REFERENCE TO RELATED APPLICATIONS

This application claims the benefit of U.S. Provisional Application Ser. No. 63/025,584, filed on May 15, 2020, and U.S. Provisional Application Ser. No. 62/942,857, filed on Dec. 3, 2019. The entire disclosures of the above applications are hereby incorporated herein by reference.

FIELD

The present disclosure relates to holographic augmented reality applications and, more particularly, medical applications employing holographic augmented reality.

Introduction

This section provides background information related to the present disclosure which is not necessarily prior art.

Ultrasound guidance has become a standard practice for many needle-based medical procedures such as needle biopsy and regional anesthesia. The use of ultrasound guidance has been shown to increase the safety and success of these procedures. However, difficulties in positioning and orienting the needle can occasionally lead to incorrect identification of the needle tip, where the needle may undesirably pass through or fall short of certain anatomical features or locations.

Certain technologies can be used to help a practitioner align the needle with confidence. These technologies range from simple mechanical devices to advanced automated needle-detection software. One particular technology involves a mechanical ultrasound needle guides that is a physical apparatus that is attached to the ultrasound probe with the purpose of guiding the needle on a trajectory visible in ultrasound images. In particular, the physical ultrasound need guide can be affixed to an ultrasound probe, typically with a reusable bracket disposed over the transducer of the probe. The needle guides may be preselected and used based on a fixed or designed angle depth. Positionable needle guides can also be used that are selectable between a limited number of angles, for example, up to five (5) different predetermined angle depths to accommodate different trajectories for insertion. Typically, these physical needle guides are removably attached to the reusable bracket, which is itself coupled to the ultrasound probe.

Physical ultrasound needle guides present certain limitations, including a cost burden and limited reusability. In fact, most ultrasound needle guides are designed to be disposable. Such physical ultrasound needle guides can further require specialized ultrasound transducers that are designed to be used with the needle guides or associated brackets. Even where certain predetermined angle depths may be selected, the practitioner may not be afforded a full and unrestricted range of angle guidance with these physical needle guides.

The known needle guides are also vendor and probe specific and are typically limited to "in-plane" or "perpendicular to plane" angles. They are often criticized by experienced clinicians such as interventional radiologists because the user is constrained to the single or few angles that the mechanical guide supports, as described hereinabove. Clinicians desire the flexibility to move the probe around independent of the guide, often needing to orient the needle out-of-plane from the probe intraprocedurally for the best visibility.

Holographic augmented reality technology is finding more widespread use in healthcare applications to improve medical procedures, clinical outcomes, and long-term patient care. These augmented reality technologies are also useful for enhancing the real environments in the patient care setting, for example, with content-specific information to improve patient outcomes. For example, a practitioner can view additional information in the same field of view while performing a medical procedure, where the practitioner does not have to change their gaze, which may slow down or reduce the efficiency of the procedure.

Accordingly, there is a continuing need for an ultrasound needle guide system and method that is cost-effective, minimizes medical waste, and provides the practitioner with a full and unrestricted range of angle guidance for optimizing percutaneous surgical procedures. Desirably, the system and the method involve holographic augmented reality and can be used with any type of ultrasound transducer.

SUMMARY

In concordance with the instant disclosure, a holographic augmented reality ultrasound needle guide system and method that is cost-effective, minimizes medical waste, and provides the practitioner with a full and unrestricted range of angle guidance for optimizing percutaneous surgical procedures, and which can be used with any type of ultrasound transducer, has been surprisingly discovered.

In one embodiment, a holographic augmented reality ultrasound needle guide system for guiding percutaneous insertion of a needle by a user into a patient includes an augmented reality display. The augmented reality display is configured to depict a virtual ultrasound image of a portion of the patient. The augmented reality display is also configured to depict a holographic needle guide on the patient based upon the selection of a reference point in the virtual ultrasound image.

In another embodiment, a method of using the holographic augmented reality ultrasound needle guide system may include a step of providing an augmented reality display, where the augmented reality display is configured to depict a virtual ultrasound image of a portion of the patient. The augmented reality display is also configured to depict a holographic needle guide on the patient based upon the selection of a reference point in the virtual ultrasound image. The method may include a step of selecting the reference point in the virtual ultrasound image of the portion of the patient. Then, the method may include a step of displaying the holographic needle guide on the patient based upon the selection of the reference point in the virtual ultrasound image of the portion of the patient. Afterwards, the method may include a step of percutaneously inserting the needle along a trajectory of the holographic needle guide.

In a further embodiment, systems and methods of the present disclosure allow for holographic display of an intended needle trajectory by using spatial computing, augmented reality, and artificial intelligence (AI) to produce a holographic light ray to mimic intended trajectory of a physical needle guide. Such systems and methods may be used with any augmented reality display and optionally use electromagnetic or optical tracking. This permits for the holographic needle guide to be adapted to any ultrasound probe by design, adjusted to any desired angle, and sized to accommodate any desired needle or trocar size.

In certain embodiments, the systems and the methods of the present disclosure can include a unique combination of ultrasound technology with holography. At least one reference point may be selected on a virtual ultrasound image, and this reference point allows a user to actively change the angle of the virtual/holographic needle guide that is generated by the system relative to an anatomy of a patient. The system may include an otherwise conventional ultrasound probe, which may have known coordinates, a gyro, and position sensors (e.g., using gyroscopes and accelerometers in the probe). The ultrasound image can include one or more pre-recorded ultrasound images or may include a virtual ultrasound image obtained in real time.

Various embodiments of the present disclosure can include the following aspects. In operation, the needle guide that would conventionally be a physical bracket can be "ghosted" or superimposed into the view of the practitioner wearing the holographic visualization system such as a Microsoft HoloLens® headset, as one non-limiting example. This allows the practitioner to perform a needle insertion at any desired angle and without the need of additional, disposable, physical needle guides. Ultrasound or EM tracking of the needle may also be employed and relayed to the practitioner through the holographic visualization system. The system may also generate error bars or an associated zone of acceptable placement that may be associated with the insertion of the needle in a specific procedure.

It should be appreciated that the use of the system and method of the present disclosure allows for improved needle visualization, reduced procedure time, more confident clinical outcome, and a desirable elimination of any physical ultrasound needle guide, bracket, or need for sterilization in the operating theater. Critical structure avoidance for minimization of non-target injuries is also provided. Advantageously, the system and method of the present disclosure may be used for a wide variety or medical procedures including, but not limited to nerve block, regional anesthesia, vascular access, biopsy, ablation, endocavity, transvaginal, transrectal for out of plane, bi-plane, curved path, straight path in-plane needle guidance at any variable or fixed angle. The system and method are also especially well adapted for use in mammography and related procedures.

In yet other embodiments, the system and method of the present disclosure addresses the limitations of mechanical needle guides by offering a holographic needle guide that supports virtually any trajectory or angle which can all easily be achieved intraprocedurally. The holographic needle guide is visible through a stereographic or stereoscopic head mounted display such as the Microsoft HoloLens® or other augmented reality device. The holographic needle guide is interactable by the user, is not constrained to the probe, but has the ability to similarly guide the proceduralist's needle at any user-defined trajectory to a user-defined destination or target.

It should be understood that the holographic needle guide offers a superior guide to the mechanical guides and has the potential to replace them in the marketplace. Instead of attaching a physical guide to the probe, the user instead dons a mixed reality headset running the application of the present disclosure.

In particular embodiments, the system and method is initiated by the user choosing a target destination for the needle guide on the ultrasound plane. Once set, the holographic target is transformed to real-word space inside the patient. A full needle guide is instantiated at that real-world position and the user then proceeds to position the holographic guide while simultaneously moving the ultrasound probe to produce any desired view.

Typically, it is desirable that the ultrasound plane be "swept" up and down the guide, offering visibility into anatomy surrounding the needle guide in all directions. This sweeping is not possible with a mechanical guide and is one of the primary reasons the mechanical guides loose favor with experienced proceduralist.

Practitioners need both of their hands when performing ultrasound guided needle procedures. As such, allowing stamping of holographic targets, needle guides and ultrasound probe positions affords them to put a tool (e.g., a needle or probe) down and then come back and know where they wanted to insert the needle based on a known and determined probe position and anatomical target.

Further areas of applicability will become apparent from the description provided herein. It should be understood that the description and specific examples are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 10A and 10B are schematic views illustrating a method for generating and moving the needle insertion guide according to the present disclosure;

Figure 11A:
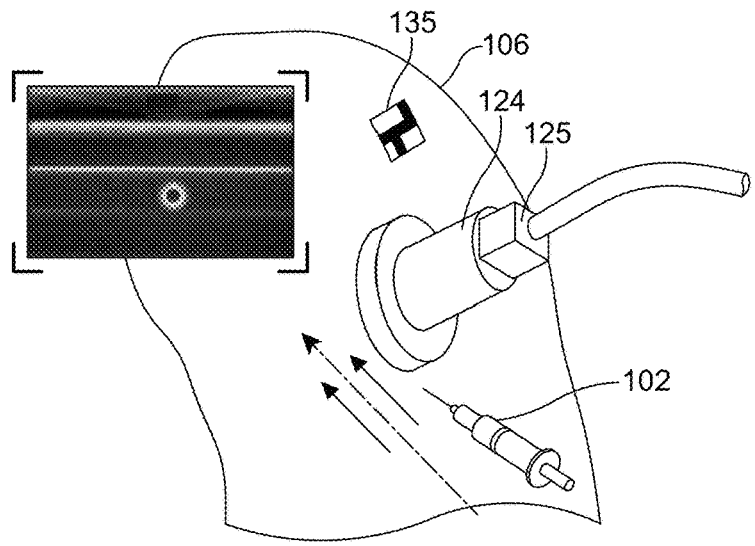
Figure 11B:
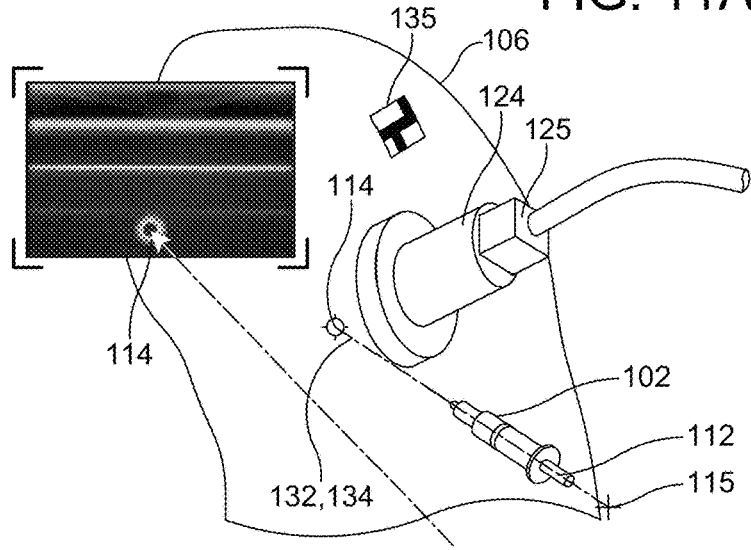
Figure 11C:
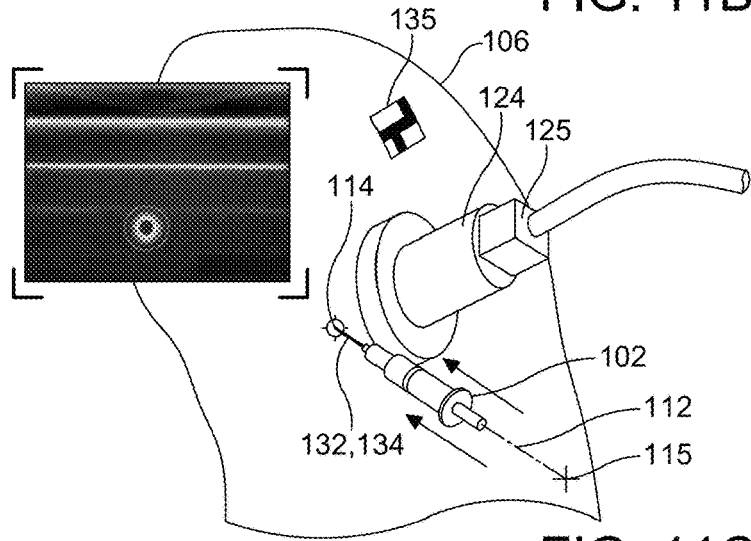
Figure 12A:
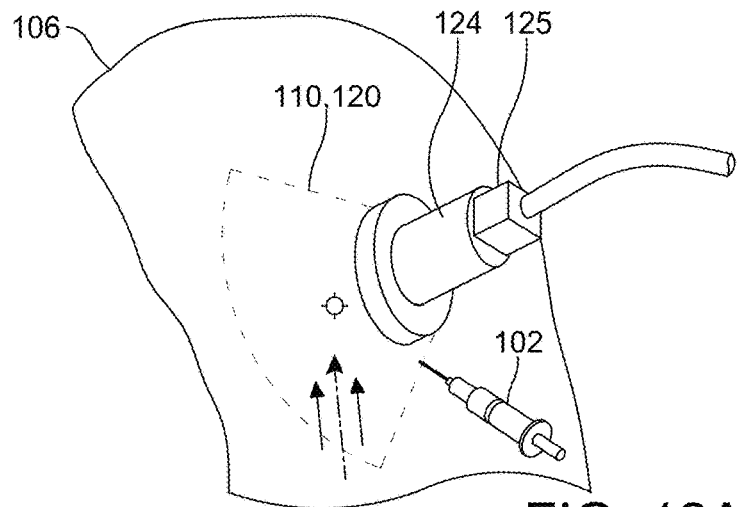
Figure 12B:
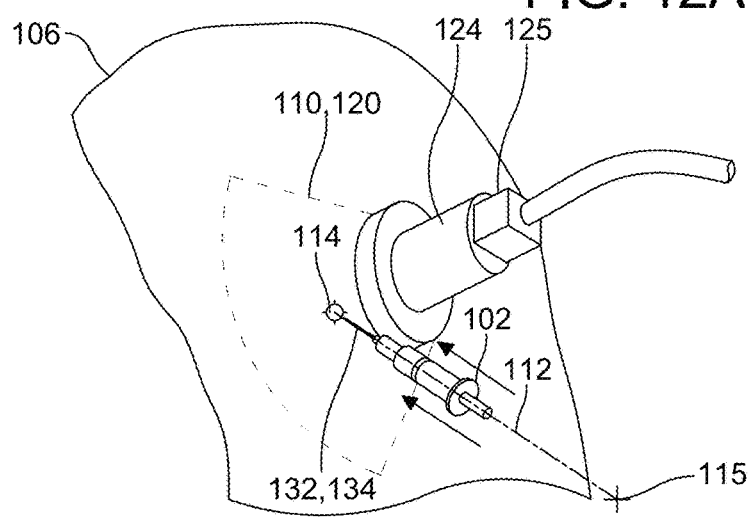
Figure 12C:
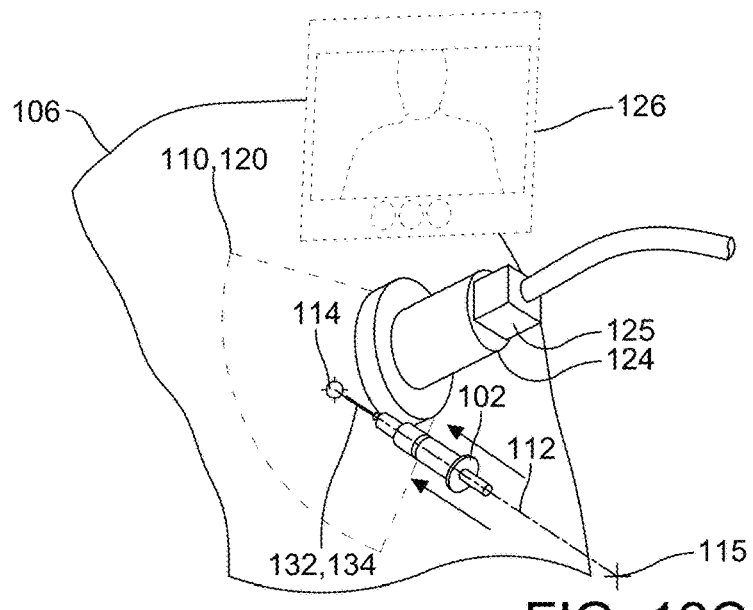
Figure 13:
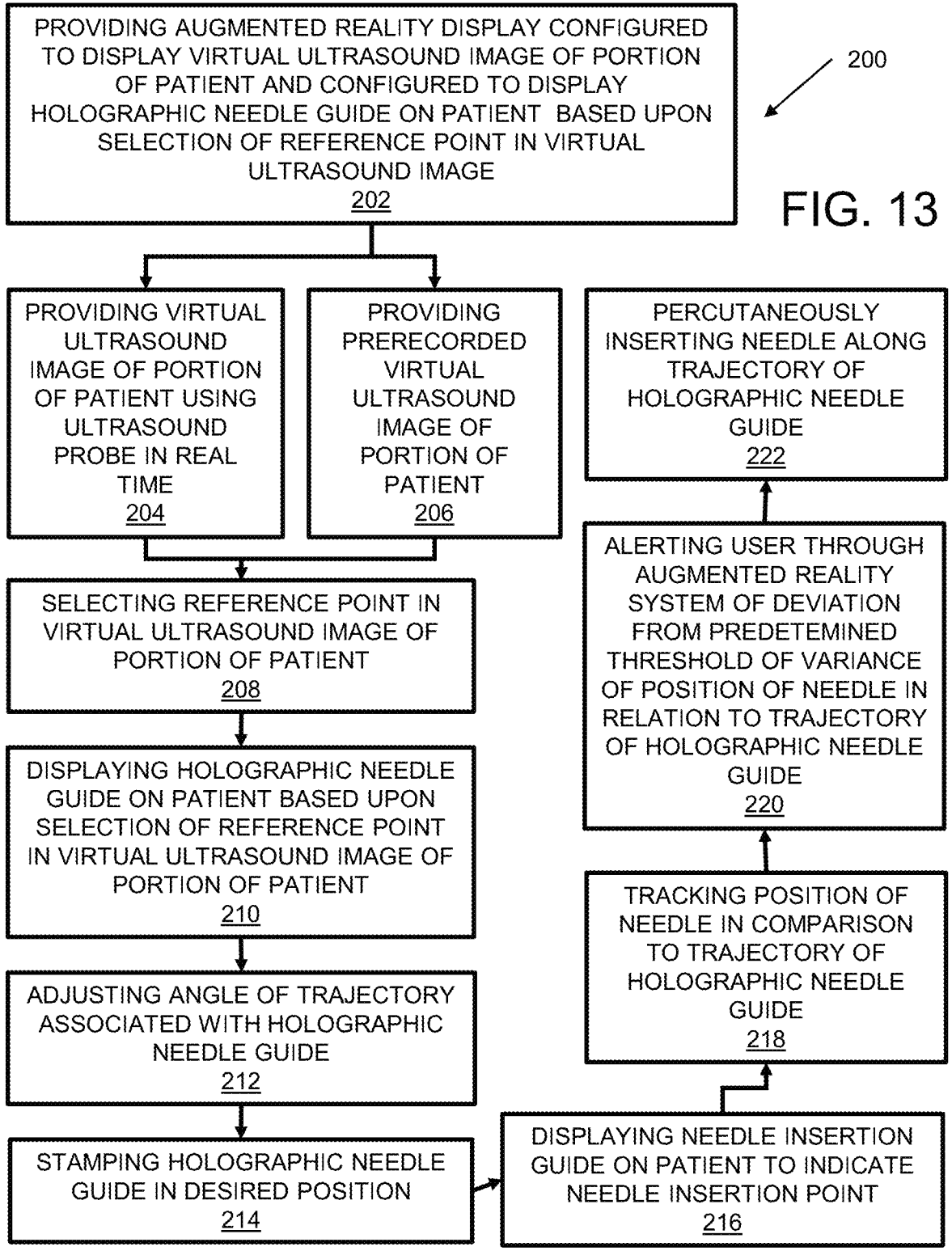

FIGS. 11A, 11B, and 11C are fragmentary perspective views illustrating a stepwise flow for needle guide targeting using a heads-up display method;

FIGS. 12A, 12B, and 12C are fragmentary perspective views illustrating a stepwise flow for needle guide targeting using a flashlight display method; and FIG. 13 is a flowchart illustrating a method for using the system in FIGS. 1-12C, according to various embodiments of the present disclosure.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments, including where certain steps can be simultaneously performed. "A" and "an" as used herein indicate "at least one" of the item is present; a plurality of such items may be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the FIGS. is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

FIGS. 1-7 illustrate a system 100 for guiding percutaneous insertion of a needle 102 by a user 104 into a patient 106 for a medical procedure. The system 100 includes an augmented reality display 108. The augmented reality display 108 is configured to depict a virtual ultrasound image 110 of a portion of the patient 106 in a mode known as heads-up display or "HUD" mode. The augmented reality display 108 is also configured to depict a holographic needle guide 112 on the patient 106 based upon the selection of a reference point 114 in the virtual ultrasound image 110, in a mode known as "Flashlight" mode. The holographic needle guide 112 may be virtually depicted in the form of an elongate axis, tube, or cylinder, as non-limiting examples, each illustrating a preferred angle of trajectory for the physical instrument. Advantageously, the system 100 is cost-effective, minimizes medical waste by elimination of the need for a physical need guide and bracket from the medical procedure, and provides the practitioner with a full and unrestricted range of angle guidance for percutaneous surgical procedures.

In one example, the system 100 may further include a computer 116 having a processor (not shown) and a memory (not shown). The memory (not shown) may have non-transitory processor-executable instructions directing the augmented reality display 108 to generate and display or depict the holographic needle guide 112 on the patient 106 based upon selection of the reference point 114 in the virtual ultrasound image 110 of the portion of the patient 106. In particular, the processor-executable instructions may permit the computer 116 to be operated in accordance with the method 200 as shown in FIG. 13.

Figure 1:
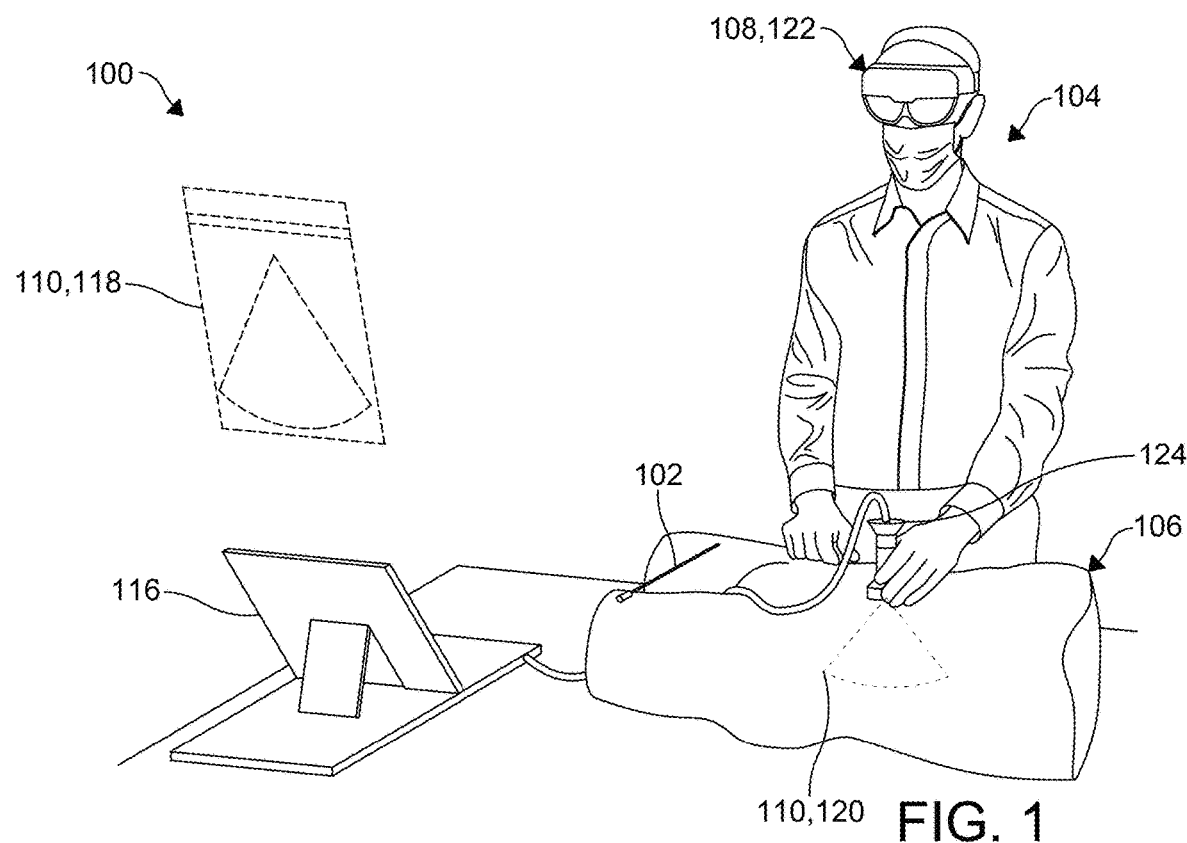
FIG. 1 is a perspective view of the holographic augmented reality ultrasound needle guide system, in operation, depicting an augmented virtual window and an augmented virtual ultrasound projection showing a virtual ultrasound scan visible through a headset display, according to one embodiment of the present disclosure.
Figure 2:
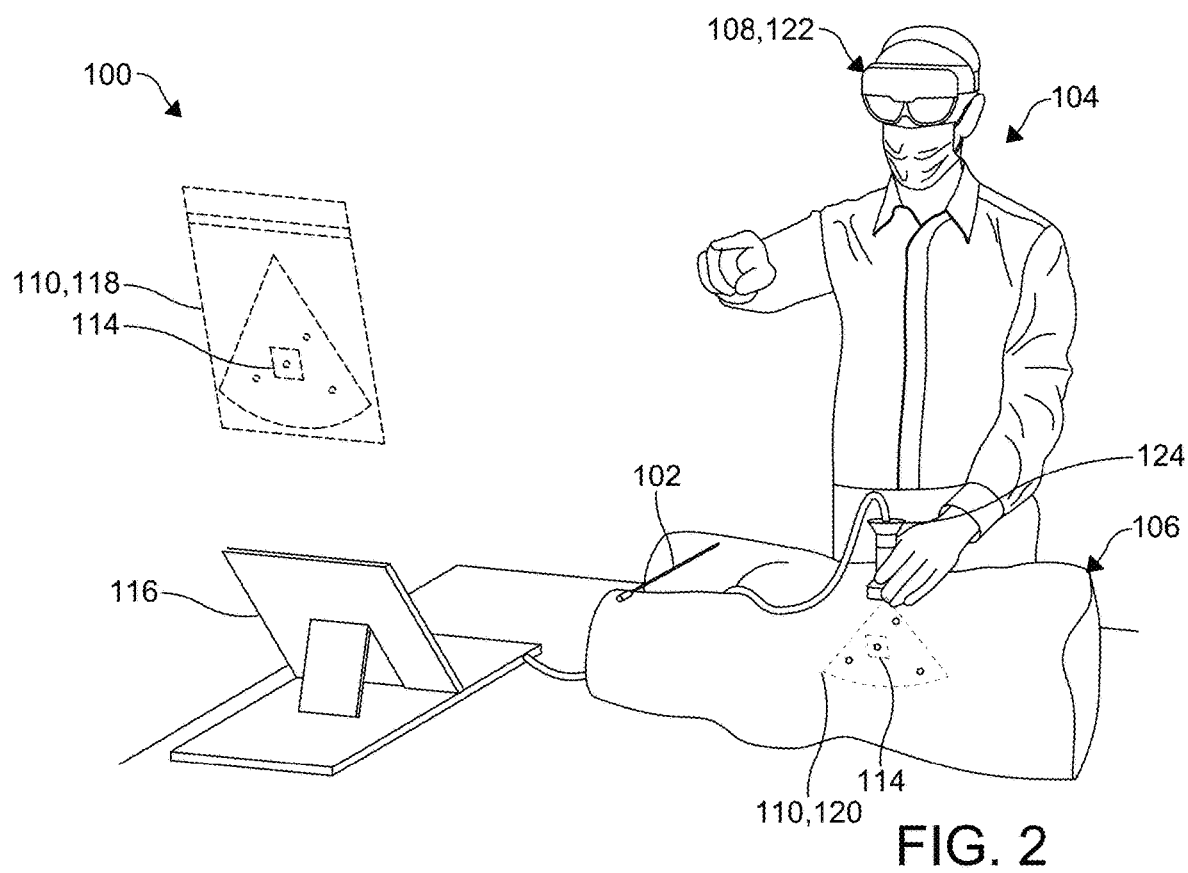
FIG. 2 is a perspective view of the system shown in FIG. 1, and depicting the user selecting a reference point on the augmented virtual window, according to one embodiment of the present disclosure.

As shown in FIGS. 1-2, the augmented reality display 108 may be configured to depict the virtual ultrasound image 110 of the portion of the patient 106 as part of a virtual window 118 and/or as part of a virtual ultrasound projection 120 on the patient 106. In a more specific example, the augmented reality display 108 may include a headset display 122 wearable by the user 104 that is in communication with the computer 116. In an even more specific example, the computer 116 may be integrated into the headset display 122 wearable by the user 104. Even more specifically, the headset display 122 may be a Microsoft HoloLens® having a tracking system (e.g., inertial measurement unit), integrated CPU and holographic processing unit, camera, and holographic projection lenses, for example, as described in U.S. Patent Application Publication No. 2018/0303563 to West et al., the entire disclosure of which including definitions is hereby incorporated herein by reference. One skilled in the art may select other suitable displays within the scope of the present disclosure.

The virtual ultrasound projection 120 that is generated by the computer 116 and depicted on the patient 106 may be further defined as a virtual display of the virtual ultrasound image 110 disposed adjacent to an ultrasound probe 124. In operation, the virtual ultrasound projection 120 may be linked to the ultrasound probe 124 so that a position of the virtual ultrasound projection 120 follows a position of the ultrasound probe 124. For example, the ultrasound probe 124 may be provided with tracking means 125 (shown in FIGS. 6, 11A-11C, and 12A-12C) such as an optical tracking cube. Alternatively, the virtual ultrasound projection 120 may be stamped in a virtually locked position (not shown). More particularly, where the virtual ultrasound projection 120 is stamped in a virtually locked position (not shown), the computer 116 will not recognize the movements of the user 104 as instructions to adjust the position of the virtual ultrasound projection 120.

In a specific, non-limiting example, the virtual ultrasound projection 120 may be displayed directly above the ultrasound probe 124 in operation, for example, as shown in FIG. 2. Advantageously, the virtual ultrasound projection 120 on the patient 106 may allow the user 104 to continue viewing the patient 106 while monitoring the virtual ultrasound image 110.

Figure 6:
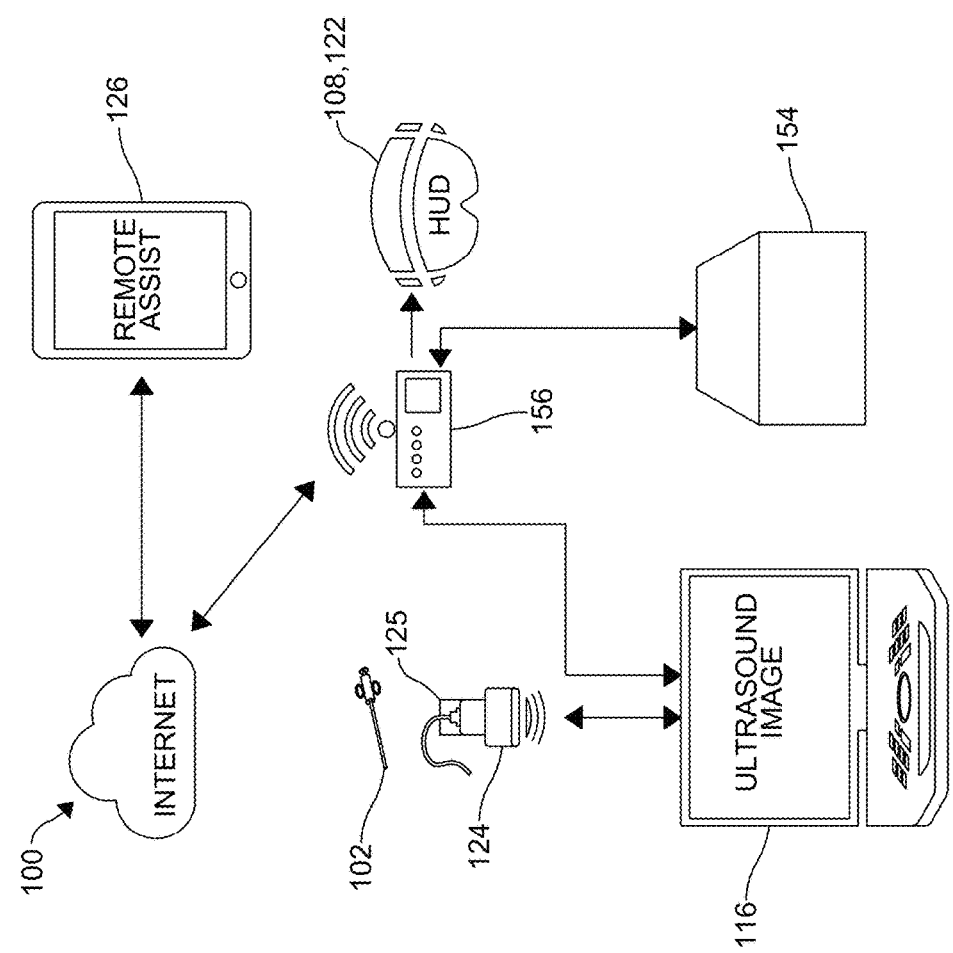
FIG. 6 is a schematic view of the system shown in FIGS. 1-5, according to another embodiment of the present disclosure.

With continued reference to FIG. 2, the virtual ultrasound image 110 may be selectable by the user 104 to identify the reference point 114. In a more particular example, for example, as shown in FIG. 6, the virtual ultrasound image 110 may also be selectable by a remote user 126 to identify the reference point 114. In an even more particular example, the remote user 126 may be located at a different site (not shown) relative to the site of the user 104 guiding the percutaneous insertion of the needle 102 into the patient 106.

Figure 3:
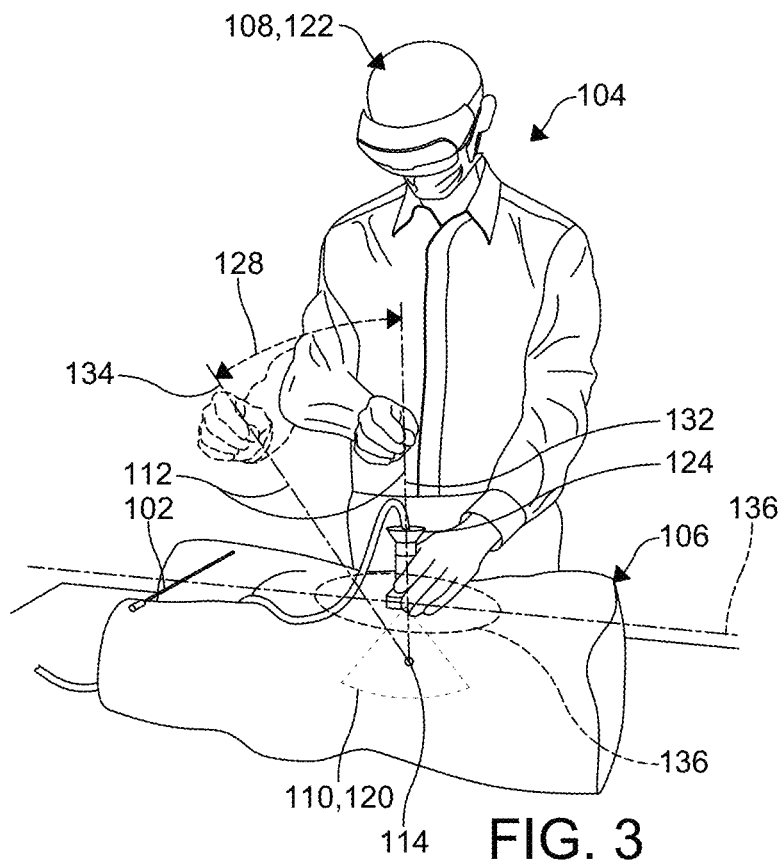
FIG. 3 is a perspective view of the system shown in FIGS. 1 and 2, and depicting the holographic needle guide being displayed and the user adjusting the trajectory of the holographic needle guide, according to one embodiment of the present disclosure.
Figure 4:
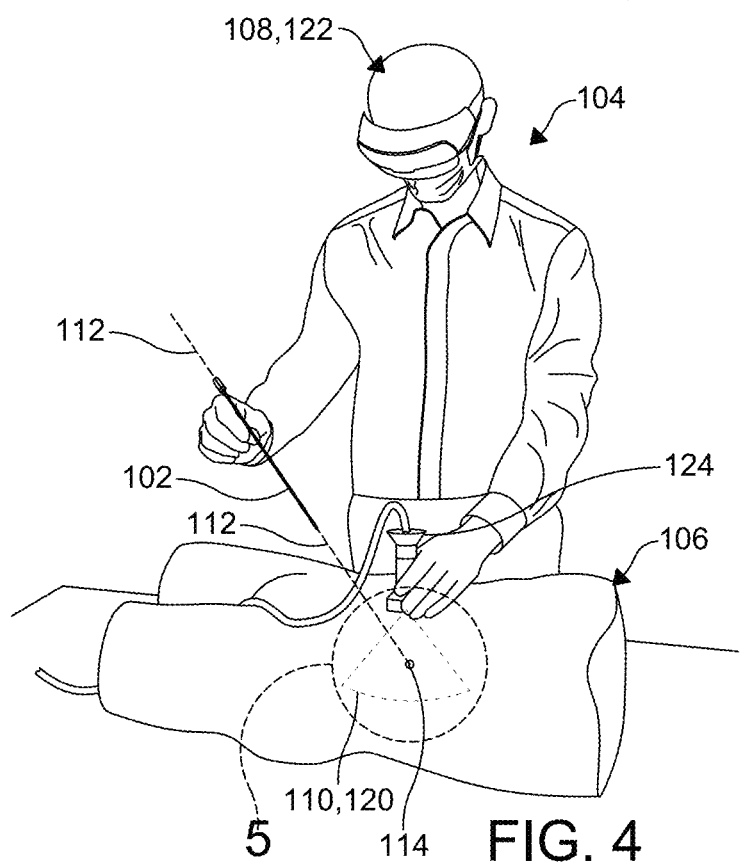
FIG. 4 is a perspective view of the system shown in FIGS. 1-3, depicting the user inserting a needle along the holographic needle guide, according to one embodiment of the present disclosure.

As shown in FIG. 3, an angle or trajectory 128 of the holographic needle guide 112 is adjustable by the user 104. In a specific example, the trajectory 128 of the holographic needle guide 112 may also be adjustable by the remote user 126. In an even more specific example, the remote user 126 may be located at a different site (not shown) from the user 104 guiding the percutaneous insertion of the needle into the patient 106. Advantageously, the user 104 and/or the remote user 126 may adjust the trajectory 128 of the holographic needle guide 112 to provide a less invasive path for the needle 102. Desirably, other nontargeted anatomical structures 130 may be more accurately and efficiently avoided by adjusting the trajectory 128 of the holographic needle guide 112.

In a particular instance, the computer 116 may be configured to define a modality or setting 132, 134 for selecting the trajectory 128 of the holographic needle guide 112, either automatically or manually within the scope of the present disclosure. In a more particular instance, the setting 132, 134 may be selected from a group consisting of an in-plane modality 132 (shown as a substantially vertical orientation in FIG. 3), an out-of-plane modality 134 (shown as the orientation set apart from the substantially vertical orientation by the angle of trajectory 128 in FIG. 3), a free hand modality (not shown), and combinations thereof.

The settings 132, 134 are based on the angle of trajectory 128 of the holographic needle guide 112 in comparison to a plane 136 associated with the patient 106. In one non-limiting example, as shown in FIGS. 3, 10A, and 10B, the plane 136 of the patient 106 may be substantially horizontal where the patient 106 is lying on an operating table, i.e., parallel with the surface of the table. The in-plane modality 132 may be described as orienting the trajectory 128 of the holographic needle guide 112 to be substantially perpendicular to the plane 136 of the patient 106. The out-of-plane modality 134 may be described as automatically orienting the trajectory 128 of the holographic needle guide 112 to a predetermined or desired angle other than the substantially perpendicular angle of the in-plane modality 132. The free-hand modality (not shown) may be used where the computer 116 does not automatically orient the trajectory 128 of the holographic needle guide 112 to a desired angle. Instead, the free-hand modality (not shown) relies on the user 104 to freely select a desired orientation for the trajectory 128 of the holographic needle guide 112.

In an even more particular instance, the holographic needle guide 112 may be depicted as a cylinder- or rod-shaped structure. The holographic needle guide 112 may depend from the selected reference point 114 and extend outwardly from the patient 106 to or through an external point 115 (shown in FIGS. 10A and 10B). The external point 115 may be a point on the plane 136, for example, such as a point on a periphery of a circle or ellipse on the plane 136 that is approximately centered on a location of the ultrasound probe 124. The external point 115 may be selected by any suitable method, including automatic selection based on algorithms configured to generate an optimum approach angle for the needle 102, or by manual selection by the user 104.

In operation, the user 104 may select the holographic needle guide 112 by grasping, pinching, tapping, and/or holding the holographic needle guide 112. While grasping, pinching, and/or holding the holographic needle guide 112, the user 104 may adjust the trajectory 128 of the holographic needle guide 112 by moving their hand with the holographic needle guide 112 to a desired position. The movement of the holographic needle guide 112 may be displayed as an arc, depending from the selected reference point 114. As shown in FIGS. 10A-10B, the movement of the holographic needle guide 112 may be correlated with a position of the ultrasound probe 124. The free-hand modality (not shown) may be further adjustable on a three dimensional setting, allowing arcs to be made in a globular pattern around the selected reference point 114. Further, the holographic needle guide 112 may be stamped in a virtually locked position (not shown). More particularly, where the holographic needle guide 112 is stamped in a virtually locked position (not shown), the computer 116 will not recognize the movements of the user 104 as instructions to adjust the position of the holographic needle guide 112. In a most particular instance, the computer 116 may have the in-plane modality 132 as a default setting. Advantageously, the user 104 may select a desirable setting 132, 134 based on the type of operation being conducted and the anatomical structures 130 of the patient 106 to more efficiently set the trajectory 128 of the holographic needle guide 112. A skilled artisan may select other suitable modalities for setting the trajectory 128 of the holographic needle guide 112, within the scope of the present disclosure.

As shown in FIGS. 1-4 and 6, the system 100 may further include the ultrasound probe 124. In a particular example, the system 100 may be configured to obtain the virtual ultrasound image 110 of the portion of the patient 106 from the ultrasound probe 124. In a more particular example, the system 100 may be configured to obtain the virtual ultrasound image 110 of the portion of the patient 106 from the ultrasound probe 124 in real time. In an alternative particular example, the virtual ultrasound image 110 of the portion of the patient 106 may be prerecorded.

In a specific example, the system 100 may also include a robotic arm (not shown). The robotic arm (not shown) may be configured to hold each of the ultrasound probe 124 and the needle 102. In a more specific example, the remote user 126 may be able to move the robotic arm (not shown) by using the computer 116. In an even more specific example, the remote user 126 may be located at a different site (not shown) from the user 104 moving the robotic arm (not shown) to perform the percutaneous insertion of the needle 102 into the patient 106. One skilled in the art may select other suitable methods of remotely performing the percutaneous insertion of the needle 102 into the patient 106, within the scope of the present disclosure.

In a specific example, the system 100 may include a tracking means (shown in FIGS. 11A-11C as 135). The tracking means may be configured to provide enhanced visualization of the anatomical structures 130 of the patient 106 and the needle 102. The tracking means may be placed on the patient 106, or on the needle 102, or both. The tracking means (not shown) may be an infrared marker (not shown), an electro-magnetic tracker (not shown), an image or model tracker (not shown), and/or an RFID tracker (not shown). As a non-limiting example, the electromagnetic tracking means (not shown) may be provided by the Aurora® tracking system, commercially available from Northern Digital Inc. As another non-limiting example, the infrared marker tracking means (not shown) may be employed with the Stylus XR® tracking system commercially available from Holo-Light GmbH. A non-limiting example of the image or model tracking means (not shown) may include the VisionLib™ tracking system commercially available from Visometry GmbH. Additionally, a non-limiting example of the RFID tracking means (not shown) may be employed with autoclavable RFID tags such as Xerafy® tags, commercially available from Xerafy Singapore Pte Ltd.

With reference to FIGS. 11A-11C, the tracking means 135 of the system 100 may include at least one optical tracking marker disposed on the patient. The optical tracking marker is configured to track the position of the body of the patient. In addition, the optical tracking marker may be further configured to spatially anchor operating information for view by the user through the headset display 108, 122. For example, where the operation projection is an ultrasound plane, the ultrasound plane may be spatially anchored to the body of the patient via the optical tracking marker. Desirably, this permits the practitioner to put the untracked instrument or needle 102 aside, while allowing the ultrasound plane to remain anchored to the body of the patient.

Nonlimiting examples of the optical tracking marker include passive markers and active markers. Passive markers may consist of retro-reflective material, which reflects incoming infrared light. Active markers may consist of infrared light emitting diodes. However, it should be appreciated that a skilled artisan may employ other types of optical tracking markers within the scope of this disclosure.

Figure 5:
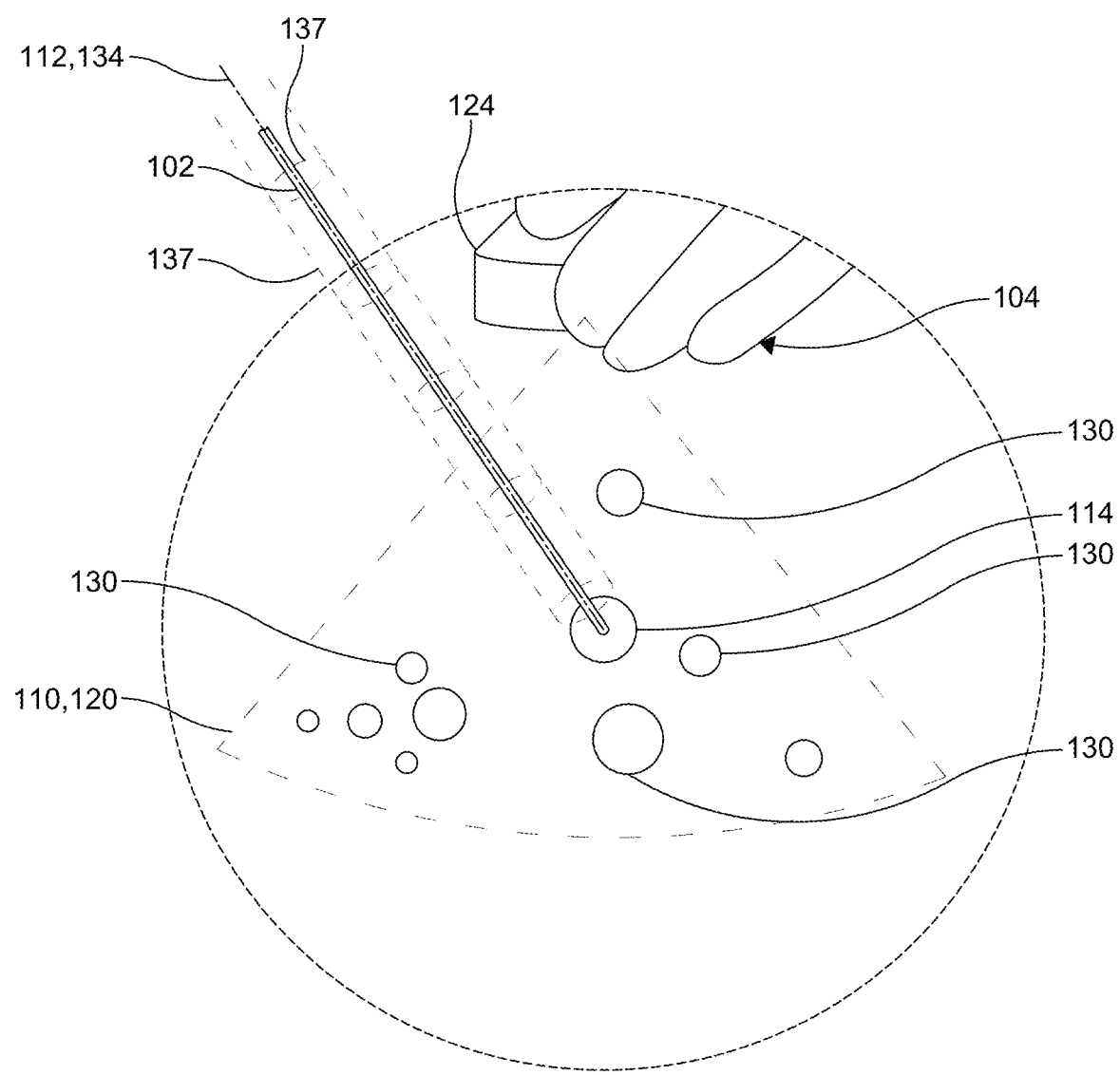
FIG. 5 is an enlarged perspective view of the user of the system taken at callout 5 in FIG. 4, shown from the point of view of the user wearing the headset display, and inserting the needle along the holographic needle guide, according to one embodiment of the present disclosure.

Referring now to FIG. 5, where the system 100 is provided with the tracking means, the augmented reality display 108 may also be configured to depict a holographic error bar 137. The holographic error bar 137 may be further configured to alert the user 104 of a deviation from a predetermined threshold of variance of a position of the needle 102 in relation to the trajectory 128 of the holographic needle guide 112. Non-limiting examples of the alert may include a visual color change, an auditory sound, a visual signal, and/or a vibration. In a particular example, the display of the holographic needle guide 112 on the patient 106 may include a minimum range (not shown) and a maximum range (not shown) dependent upon a physical characteristic of the needle 102. As a non-limiting example, the holographic needle guide 112 may be adjustable and configured to depict a physical length and a diameter of the needle 102 being inserted into the patient 106. Advantageously, by providing the holographic error bars 137 and the physical limitations of the needle 102 in the display of the holographic needle guide 112, the user 104 may more accurately, expeditiously, and confidently perform the surgery. A skilled artisan may use other methods of identifying and alerting a user 104 of a deviation from a predetermined threshold of variance of a position of the needle 102 in relation to the trajectory 128 of the holographic needle guide 112, within the scope of the present disclosure.

Figure 8:
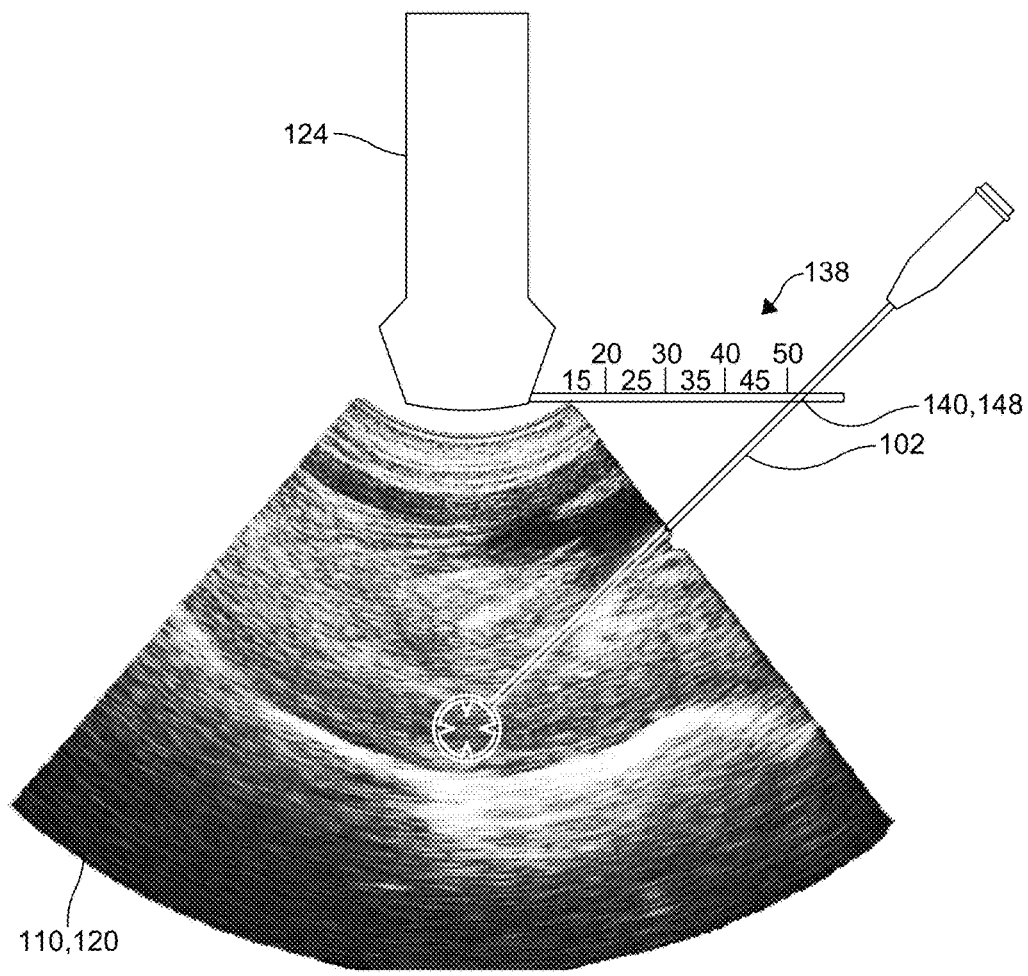
FIG. 8 is a schematic view of an ultrasound scan, and depicting the ultrasound scan with the reference point selected and displaying a virtual needle insertion point, according to one embodiment of the present disclosure.
Figures 9A, 9B:
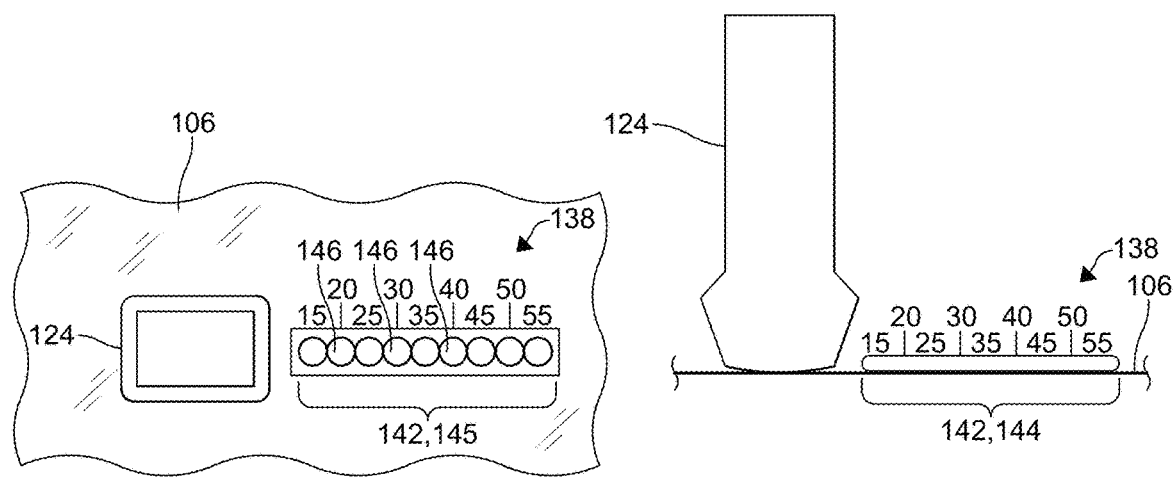
FIG. 9A is a top plan view of a needle insertion guide for determining a desired needle insertion point, and depicting a physical template with holes disposed adjacent to an ultrasound probe for use with the needle insertion guide, according to one embodiment of the present disclosure.
FIG. 9B is a side elevational view of a needle insertion guide for determining the desired needle insertion point, and depicting a physical template with measurement marks disposed adjacent to the ultrasound probe for use with the needle insertion guide, according to another embodiment of the present disclosure.

As shown in FIGS. 8, 9A, and 9B, the system 100 may include a needle insertion guide 138 for use in conjunction with the holographic needed guide 112 as described herein. The needle insertion guide 138 may be a physical device providing a visual cue on the patient 106. The needle insertion guide 138 may be configured to indicate a desirable or a predetermined needle insertion point 140, 148. In a specific example, as shown in FIGS. 9A and 9B, the needle insertion guide 138 may be a physical template 142 placed on the patient 106 near a location of the holographic needed guide 112. In a more specific example, the physical template 142 may include a bar 144 with reference markings (shown in FIG. 9B) that define adjacent to the reference markings the possible insertion points 140, or a bar 145 with a plurality of holes 146 arranged in a linear row (shown in FIG. 9A) inside of which define the possible insertion points 148, in order to give the user a further visual cue of the desirable needle insertion points 140, 148 to achieve a desired trajectory (not shown) of the needle 102 in conjunction with the holographic needed guide 112.

In an alternative example, as shown in FIG. 8, the needle insertion guide 138 may be disposed on or attached to the ultrasound probe 124. Where the needle insertion guide 138 is disposed on the ultrasound probe 124, the needle insertion guide 138 may be configured to provide a visual cue of the intended needle insertion point on the patient 106 and corresponding with the holographic needle guide 112.

As shown in FIG. 6, various components of the system 100 may be interconnected in various ways. Each of the ultrasound probe 124, the needle 102, and the needle insertion guide 138 may be in communication with the computer 116. The computer 116 may also be in communication with the augmented reality display 108. The computer 116 may also deliver and receive data from a remote user 126, for example, thorough a terminal or external computer of the remote user 126 in communication with the computer 116 over a wide area network such as the Internet. The communication may be provided through suitable wired or wireless technology means. Internet connected devices (not shown) may also be utilized to further provide the aforementioned communications. A skilled artisan may select other suitable methods to interconnect and provide communications within the system 100, within the scope of the present disclosure.

Figure 7:
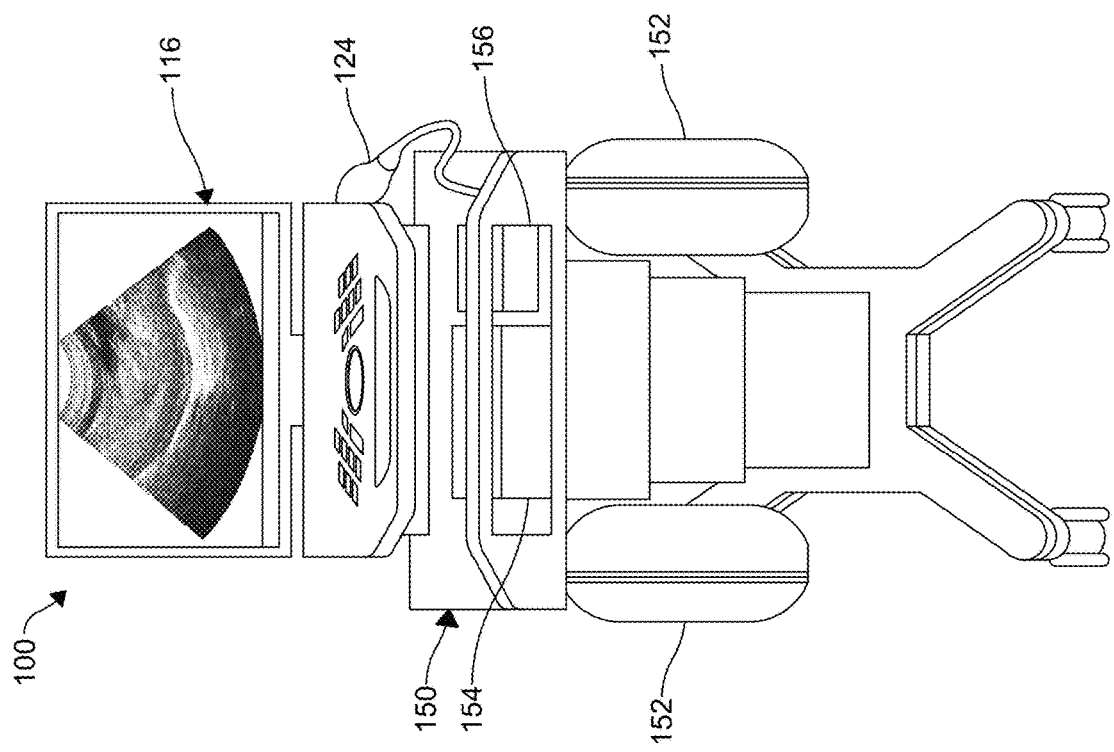
FIG. 7 is a front elevational view of the system shown in FIGS. 1-6, depicting the system disposed on a movable cart, according to a further embodiment of the present disclosure.

As shown in FIG. 7, the various components of the system 100 may be provided together on a movable cart 150. The cart 150 may include each of the computer 116, the augmented reality display 108, and the ultrasound probe 124. The cart 150 may store the augmented reality display 108 in a case 152 for enhanced protection from damage. Where the computer 116 is provided on the cart 150, the computer 116 may also include an external server 154 and an external wireless router 156 with which the computer 16 is in communication. Advantageously, the cart 150 may more easily permit a user 104 to move the system 100 to a location (not shown) of the patient 106 for the medical procedure.

As shown in FIG. 13, the present technology includes methods 200 of using the holographic augmented reality ultrasound needle guide systems 100 described herein. The method 200 may include a step 202 of providing an augmented reality display 108. The augmented reality display 108 may be configured to depict a virtual ultrasound image 110 of a portion of the patient 106. The augmented reality display 108 may also be configured to depict a holographic needle guide 112 on the patient 106 based upon the selection of a reference point 114 on the virtual ultrasound image 110. The method 200 may also include a step 204 of providing the virtual ultrasound image 110 of a portion of the patient 106 using an ultrasound probe 124 in real time. Desirably, the real time imaging provided by the ultrasound probe 124 may enable more accurate visualization of the anatomical structures 130 of the patient 106. Alternatively, the method 200 may include a step 206 of providing a prerecorded virtual ultrasound image 110. Advantageously, where the virtual ultrasound image 110 is prerecorded, the user 104 may not be required to hold the ultrasound probe 124 while also adjusting the trajectory 128 of the holographic needle guide 112.

The method 200 may include a step 208 of selecting the reference point 114 in the virtual ultrasound image 110 of the portion of the patient 106. Subsequently, the method 200 may include a step 210 of displaying the holographic needle guide 112 on the patient 106 based upon the selection of the reference point 114 on the virtual ultrasound image 110 of the portion of the patient 106.

With continued reference to FIG. 13, the method 200 may further include a step 212 of adjusting the angle of trajectory 128 associated with the holographic needle guide 112 after displaying the holographic needle guide 112 on the patient 106. In a particular example, the computer 116 may include a setting 132, 134 for automatically selecting the trajectory 128 of the holographic needle guide 112. The setting 132, 134 may be selected from an in-plane modality 132, an out-of-plane modality 134, and/or a free hand modality (not shown).

As shown in FIG. 13, the method 200 may include a step 214 of stamping the holographic needle guide 112 in a desired position after adjusting the angle of trajectory 128 associated with the holographic needle guide 112. Where the user 104 may need both of their hands when performing ultrasound guided needle procedures, the holographic needle guide 112 may be stamped in a virtually locked position (not shown). More particularly, where the holographic needle guide 112 is stamped in a virtually locked position (not shown), the computer 116 will not recognize the movements of the user 104 as instructions to adjust the trajectory 128 of the holographic needle guide 112. In an even more particular example, the computer 116 may allow each of the reference point 114, the holographic needle guide 112, the virtual ultrasound projection 120, and combinations thereof to be stamped in virtually locked positions (not shown). Advantageously, the stamping feature affords the user 104 to put the needle 102 or the ultrasound probe 124 down and then come back and know where they wanted to insert the needle 102 based on holographic needle guide 112 and the reference point 114.

As further shown in FIG. 13, the method 200 may include a step 216 of displaying a needle insertion guide 138 on the patient 106 to indicate a needle insertion point 140, 148 after displaying the holographic needle guide 112. Then, the method 200 may include a step 218 of tracking a position of the needle 102 in comparison to the trajectory 128 of the holographic needle guide 112 after inserting the needle 102 along the holographic needle guide 112. As shown in FIG. 5, where the position of the needle 102 is tracked, the method 200 may have another step 220 of alerting the user 104 through the augmented reality display 108 of a deviation from a predetermined threshold of variance of a position of the needle 102 in relation to the trajectory 128 of the holographic needle guide 112 after inserting the needle 102 along the holographic needle guide 112. Afterwards, the method 200 may include a step 222 of percutaneously inserting the needle along a trajectory 128 of the holographic needle guide 112.

Examples

The system 100 and method 200 of the present disclosure can further be described as a unique combination of ultrasound technology with holography, which can be further illustrated in view of the following non-limiting examples described with general reference to FIGS. 10A-10B, 11A-11C, and 12A-12C.

Needle Guide Object:

In a particular example, the needle guide is defined as being a line between two points. The visual target is located at the distal tip of the line. There is also a ghosted geometry at the proximal end of the line, resembling the fixture to connect the physical needle to the physical guide.

Interactions:

In certain examples, the target may not be an interactable. The fixture geometry may be interactable and may perform translation-only (i.e., no rotation or scaling). The fixture may support both far and near interactions as defined by the Microsoft Mixed Reality Toolkit (MRTK). For "far interaction," the user may select the fixture by pointing a hand ray at the handle and then performing a pinch-and-hold. While pinched, the fixture may be transformed through hand gestures. For "near interaction," the system may support direct manipulation of the fixture via existing patterns in the MRTK. Interaction states of the fixture may follow the MRTK patterns, for example, as described in the MRTK Interactable Feature Overview (found at https://microsoft.github.io/MixedRealityToolkit-Unity/Documentation/README_Interactable.html, last accessed Nov. 27, 2020). The interact states include: i) Default (normal, observation); ii) Focused (targeted, hover). e.g. the fixture may light up; and iii) Active (pressed) (grabbed vs. ungrabbed)—fixture changes color to blue.

Visual Specification of Needle Guide:

In particular examples, the line may be rendered as a cylinder without end caps. This could also include a native line, if issues arise with rendering a cylinder. The cylinder's material may be a whitish x-ray shader. There may be front-facing rendering-only on the cylinder. The target may be a billboard shape. The fixture may be a translucent, green, x-ray shader, resembling the real-world plastic object. The scale of each of the needle guide features can be as follows: i) target, one and half (1.5) cm diameter; ii) cylinder, a quarter (0.25) cm diameter; and iii) fixture, about three (3) cm in length.

Needle Guide Targeting:

In yet other examples, a near cursor on the user's index finger may be the default MRTK cursor. Targeting may be possible on both the heads-up display (HUD), as shown in FIGS. 11A-11C, and the flashlight ultrasound planes, as shown in FIGS. 12A-12C. Targeting may support eye-gaze, hand-ray (far) and direct manipulation (near). When the HUD or flashlight plane is targeted/hovered, the cursor may visually change to targeting/hover state. Flashlight mode can be toggled on and off. The HUD can be toggled on and off.

The user may then commit a target location by one of the following: i) far interaction, where the user extends arm, aims hand-ray, and either AirTaps or says the "Set target" voice command; or ii) near interaction, where the user presses the HUD or flashlight ultrasound plane directly with their index finger.

Upon committing the target location, the following may happen. First, a visual indication may occur on the ultrasound plane (either HUD or flashlight or both simultaneously) making it clear that an action was received (e.g. shockwave). Second, the committed target visual on the HUD or flashlight plane may fade away as soon as it's committed. Third, the target location on the HUD or flashlight plane may be transformed to world space. Fourth, the needle guide may appear in the scene. Fifth, the distal tip of the needle guide may be initialized at the target location. Sixth, the same visual indicator (e.g. shockwave) may occur when the target is initialized in 3D space. Seventh, the direction of the needle guide may be determined by the ultrasound plane and may be "in-plane" when initialized. Eighth, the proximal fixture on the needle guide's cylindrical shaft may default to about 4 cm "above" the transducer probe (i.e., outside the patient) so the user can easily grab it.

The user may be permitted to "re-target" at any time on the HUD or flashlight planes. If a target is committed on the HUD it can automatically be populated on the flashlight mode and vice versa. The user can lock and stamp in a target and holographic needle guide in physical space and reference that relative to the optical tracking marker on the patient (shown in FIGS. 11A-11C and 12A-12C) to account for movement between the patient and ultrasound probe. The user can lock and stamp the position of an ultrasound probe in physical space and reference that relative to the optical tracking and targeting and holographic needle guide by referencing an optical maker on the patient Advantageously, the ultrasound needle guide system 100 and method 200 are cost-effective, minimizes medical waste, and provides the practitioner with a full and unrestricted range of angle guidance for percutaneous surgical procedures. Importantly, the system 100 and related method 200 involves holographic augmented reality and can be used with any type of ultrasound transducer.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A system for guiding percutaneous insertion of a needle by a user into a patient, comprising:
    an augmented reality display configured to depict a virtual ultrasound image of a portion of the patient and configured to depict a holographic needle guide on the patient based upon selection of a reference point in the virtual ultrasound image;
    a physical ultrasound probe;
    a physical needle insertion guide disposed on the physical ultrasound probe and configured to indicate at least one predetermined insertion point on the patient to the user, wherein the physical needle insertion guide is a physical template configured to be placed on the patient; and
    a computer having a processor and a memory, the memory including non-transitory processor-executable instructions directing the augmented reality display to display the holographic needle guide on the patient based upon selection of the reference point in the virtual ultrasound image of the portion of the patient, the holographic needle guide displaying a trajectory for the needle to the reference point wherein the trajectory is independent of a position of the needle, wherein the holographic needle guide is adjustable in real-time during the procedure by at least one of the user and a remote user, and after adjustment the holographic needle guide is configured to be stamped in a virtually locked position.

2. The system of claim 1, wherein the augmented reality display is configured to depict the virtual ultrasound image of the portion of the patient as a member selected from a group consisting of a virtual window, a virtual ultrasound projection on the patient, and a combination thereof.

3. The system of claim 1, wherein the augmented reality display includes a headset display wearable by the user.

4. The system of claim 3, wherein the computer is integrated into the headset display wearable by the user.

5. The system of claim 1, wherein the virtual ultrasound image is selectable to identify the reference point by at least one of the user and a remote user located at a different site from the user and guiding the percutaneous insertion of the needle into the patient.

6. The system of claim 1, wherein the system is configured to obtain the virtual ultrasound image of the portion of the patient from the ultrasound probe in one of real time and as a prerecorded image.

7. The system of claim 1, wherein the physical needle insertion guide is configured to provide a virtual needle insertion point as the at least one predetermined insertion point on the patient.

8. The system of claim 1, further comprising tracking means configured to provide enhanced visualization of at least one of an anatomy of the patient and the needle, the tracking means selected from a group consisting of an infrared marker, an electro-magnetic tracker, an optical tracker, and combinations thereof.

9. The system of claim 1, wherein the augmented reality display is configured to depict a holographic error bar adjacent the holographic needle guide, the holographic error bar configured to alert the user of a deviation from a predetermined threshold of variance of a position of the needle in relation to a trajectory of the holographic needle guide.

10. The system of claim 1, wherein an adjustment to the holographic needle guide depicts a physical length and a diameter of the needle.

11. The system of claim 1, wherein the physical needle insertion guide includes a bar having a plurality of holes arranged in a linear row to depict possible insertion points.

12. The system of claim 1, wherein the holographic needle guide is adjustable by one of the user or the remote user directly moving the holographic needle guide to a desired position.

13. The system of claim 12, wherein after stamping the computer will not recognize movements of the user as instructions to adjust the position of the holographic needle guide.

14. A method for performing a surgical procedure, which includes percutaneous insertion of a needle by a user into a patient, the method comprising the steps of:
providing a system for guiding percutaneous insertion of a needle by a user into a patient including:
an augmented reality display configured to depict a virtual ultrasound image of a portion of the patient and configured to depict a holographic needle guide on the patient based upon selection of a reference point in the virtual ultrasound image,
a physical ultrasound probe,
a physical needle insertion guide disposed on the physical ultrasound probe and configured to indicate at least one predetermined insertion point on the patient to the user, wherein the physical needle insertion guide is a physical template configured to be placed on the patient, and
a computer having a processor and a memory, the memory including non-transitory processor-executable instructions directing the augmented reality display to display the holographic needle guide on the patient based upon selection of the reference point in the virtual ultrasound image of the portion of the patient, the holographic needle guide displaying a trajectory for the needle to the reference point wherein the trajectory is independent of a position of the needle, wherein the holographic needle guide is adjustable in real-time during the procedure by at least one of the user and a remote user;
selecting the reference point in the virtual ultrasound image of the portion of the patient;
displaying the holographic needle guide on the patient based upon the selection of the reference point in the virtual ultrasound image of the portion of the patient;
adjusting an angle of trajectory associated with the holographic needle guide;
stamping in augmented reality the holographic needle guide in a desired position; and
percutaneously inserting the needle along a trajectory of the holographic needle guide.

15. The method of claim 14, further comprising a step of providing the virtual ultrasound image of a portion of the patient using the physical ultrasound probe in one of real time and as a prerecorded image.

16. The method of claim 14, further comprising a step of tracking a position of the needle in comparison to the trajectory of the holographic needle guide after inserting the needle along the holographic needle guide.

17. The method of claim 14, further comprising alerting the user through the augmented reality display of a deviation from a predetermined threshold of variance of a position of the needle in relation to the trajectory of the holographic needle guide after inserting the needle along the holographic needle guide.

18. The method of claim 14, further comprising a step of providing a physical needle insertion guide for displaying a visual cue on the patient to indicate a needle insertion point after displaying the holographic needle guide.

* * * * *